(12) United States Patent
Chen et al.

(10) Patent No.: US 7,228,878 B2
(45) Date of Patent: Jun. 12, 2007

(54) CATHETER TUBING WITH IMPROVED STRESS-STRAIN CHARACTERISTICS

(75) Inventors: John Jianhua Chen, Plymouth, MN (US); Douglas A. Devens, Jr., St. Paul, MN (US); Paul James Miller, Vadnais Heights, MN (US); Edward Parsonage, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 860 days.

(21) Appl. No.: 10/309,466

(22) Filed: Dec. 4, 2002

(65) Prior Publication Data

US 2004/0109966 A1 Jun. 10, 2004

(51) Int. Cl.
*F16L 9/14* (2006.01)
*A61M 25/00* (2006.01)

(52) U.S. Cl. ............ 138/141; 138/137; 138/140; 138/172; 604/524

(58) Field of Classification Search .......... 138/141, 138/137, 140, 172, 174; 604/524, 525
See application file for complete search history.

(56) References Cited

U.S. PATENT DOCUMENTS

| | | | |
|---|---|---|---|
| 3,825,036 A | 7/1974 | Stent | |
| 3,924,632 A * | 12/1975 | Cook | 604/527 |
| 4,250,072 A | 2/1981 | Flynn | |
| 4,547,193 A * | 10/1985 | Rydell | 604/524 |
| 4,796,629 A | 1/1989 | Grazel | |
| 5,254,107 A | 10/1993 | Soltesz | |
| 5,290,230 A | 3/1994 | Ainsworth et al. | |
| 5,312,356 A | 5/1994 | Engelson et al. | |
| 5,456,674 A | 10/1995 | Bos et al. | |
| 5,533,985 A | 7/1996 | Wang | |
| 5,658,251 A | 8/1997 | Ressemann et al. | |
| 6,066,114 A | 5/2000 | Goodin et al. | |
| 6,290,692 B1 | 9/2001 | Klima et al. | |
| 6,688,339 B2 * | 2/2004 | Yamaguchi et al. | 138/129 |
| 6,689,120 B1 * | 2/2004 | Gerdts | 604/526 |
| 2002/0081404 A1 | 6/2002 | Schaible et al. | |
| 2002/0132076 A1 | 9/2002 | Stevens | |

FOREIGN PATENT DOCUMENTS

WO    WO 01/34062    5/2001

* cited by examiner

*Primary Examiner*—Patrick F. Brinson
(74) *Attorney, Agent, or Firm*—Miller, Matthias & Hull

(57) ABSTRACT

A medical tubing is disclosed which includes a first material extending between proximal and distal ends of the tubing and which defines a lumen of the tubing. The tubing also includes a second material extending between at least portion of the distance between the proximal and distal ends of the tubing and that is embedded in the first material. The second material is fractured. The first material is flexible and the second material is relatively rigid and brittle and the two materials combined to provide a medical tubing that exhibits strain softening behavior.

23 Claims, 3 Drawing Sheets

CATHETER TUBING WITH IMPROVED STRESS-STRAIN CHARACTERISTICS

BACKGROUND

1. Technical Field

An improved intravascular catheter is disclosed. More specifically, an improved catheter is disclosed that provides improved stress-strain behavior that exhibits a sufficient degree of stiffness at low cross-axial strains for sufficient pushability, and sufficient flexibility at higher cross-axial strains for sufficient trackability.

2. Description of the Related Art

Intravascular catheters are widely used for a variety of diagnostic and therapeutic purposes. Specifically, angioplasty has been developed as an alternative to bypass surgery for treating vascular diseases or other conditions that occlude or reduce blood flow in a patient's vascular system. Balloon angioplasty has proven to be a useful and often a preferred treatment for coronary diseases that cause blockages, also known as stenosis, in coronary arteries as well as other parts of the vascular system.

Advancing the catheter assembly to position the balloon across a stenosis can be a difficult and time consuming task due to the narrow and tortuous vascular passages through which the catheter assembly must be passed. The balloon must be positioned precisely and movement of the balloon through the vascular system must be conducted in as atraumatic manner as possible.

To be effective, the catheter assembly preferably has two distinct features. First, the catheter assembly must have sufficient "pushability" or axial strength thereby enabling a longitudinal force to be transmitted through the assembly so that the physician can push the catheter assembly through the vascular system to the stenosis. Concurrently, the catheter assembly preferably may also be sufficiently flexible so that the catheter assembly has good "trackability" so as to enable the physician to navigate the tortuous passages of the patient's vascular system.

To satisfy these criteria, balloon catheter assemblies typically have a stiff proximal end and a more flexible distal end. If a hypotube is used at the proximal section, it is typically manufactured from a metallic material, such as stainless steel. The balloon catheter or the distal section of the assembly is typically manufactured from a more flexible, polymer product. Thus, the hypotube is relatively stiff, enabling the assembly to have good pushability while the balloon catheter or tube is more flexible, enabling the assembly to have sufficient trackability.

One problem associated with connecting a relatively stiff tubular member, such as a hypotube, to a more flexible tubular member, such as the catheter, is that the transition between the stiff hypotube and the more flexible catheter can result in kinking which can close the lumen of the hypotube or the lumen of the catheter thereby blocking flow through these lumens to the balloon.

To solve this problem, stiffening members have been provided which help serve as a transition member between the hypotube and the catheter. Such stiffening members are disclosed in U.S. Pat. Nos. 5,658,251 and 6,066,114.

As angioplasty and stent delivery procedures continue to increase, there is a continuing need to provide new catheter systems and improved trackability and flexibility which can eliminate or reduce the need for hypotubes and stiffening members.

Returning to the competing interests of pushability and trackability, in general, the force ($F_s$) required to push a flexible shaft through a tortuous path is the sum of both the frictional forces ($F_{fr}$) and the force generated from bending the flexible shaft ($F_b$):

$$F_s = F_{fr} + F_b \quad (1)$$

where $F_b$ is related to the flexural modulas of the shaft ($E_b$). Furthermore, it is known that when the force ($F_s$) on a given length of tubing (1) exceeds a certain critical value ($F_{sc}$), the tubing will buckle or collapse and thus limit both the trackability, force transmission of the catheter and fluid communication through the catheter:

$$F_s > F_{sc} = \pi^3/4 E_b (R_o^4 - R_i^4)/l^2 \rightarrow \text{buckling} \quad (2)$$

wherein $R_1$ and $R_o$ are the inside and outside radii, respectively. As a result, a balance exists with regard to the trackability and pushability of a catheter as a function of the flexural modulus $E_b$. This balance is further illustrated in FIG. 1.

Referring to FIG. 1 at a low flexural modulus ($E_b$), the catheter will not have sufficient strength to overcome the frictional forces ($F_{fr}$), $F_s$ will exceed $F_{sc}$, and the tubing will buckle. On the other hand, at a high flexural modulus ($E_b$), the bending forces ($F_b$) within the tortuous path will be too large, $F_s$ will exceed $F_{sc}$, and sections of the tubing will buckle. In addition, a high flexural modulus ($E_b$) can produce excessive counteractive force, producing guide catheter back-out.

Accordingly, a catheter material is needed that is relatively stiff at low bending strains, yet at larger bending strains is sufficiently flexible to minimize the bending forces.

SUMMARY OF THE DISCLOSURE

An improved medical tubing is disclosed which comprises two materials including a first material that extends between a proximal end and a distal end of the tubing and which defines a lumen. The second material extends between at least a portion of the distance between the proximal and distal ends of the tubing and is embedded in the first material. The second material is fractured.

In an embodiment, the first material has a low flexural modulus and a high break elongation (or elongation @ break) and the second material has a high flexural modulus and low break elongation.

In various embodiments, the second material may comprise a layer disposed between inner and outer layers of the first material, the second material may comprise a strip along a longitudinal axis of the tubing, the second material may comprise a plurality of circumferential rings that are axially spaced apart along the tubing or the second material may comprise a plurality of domains extending along a longitudinal axis of the tubing. The second material may be blended with a third material. Other alternative embodiments and combinations of the above will apparent to those skilled in the art. Further, the second material may be provided in a non-fractured form and fractured in situ or in vivo.

A method of making a medical tubing is also disclosed which comprises the steps of co-extruding a first material having a first stiffness and a second material having a second stiffness to form a tubular shaft, the second stiffness being greater than the first stiffness. The method also includes cooling the first and second materials, stretching the first and second materials, fracturing the second material.

Another disclosed method of manufacturing a medical tubing is disclosed which comprises co-extruding a first material having a first stiffness and a second material having a second stiffness to form a tubular shaft. The second stiffness being greater than the first stiffness. Cooling the first and second materials, cutting the tubular shaft, inserting the tubular shaft into a vascular system of a patient, stretching the first and second materials in vivo as the tubular shaft travels through the vascular system thereby fracturing the second material in vivo, performing a medical procedure using the medical tubing within the vascular system, and removing the medical tubing from the patient.

An improved tubing that exhibits strain softening characteristics is disclosed herein.

DETAILED DESCRIPTION OF THE ILLUSTRATED EMBODIMENTS

Figure 1:
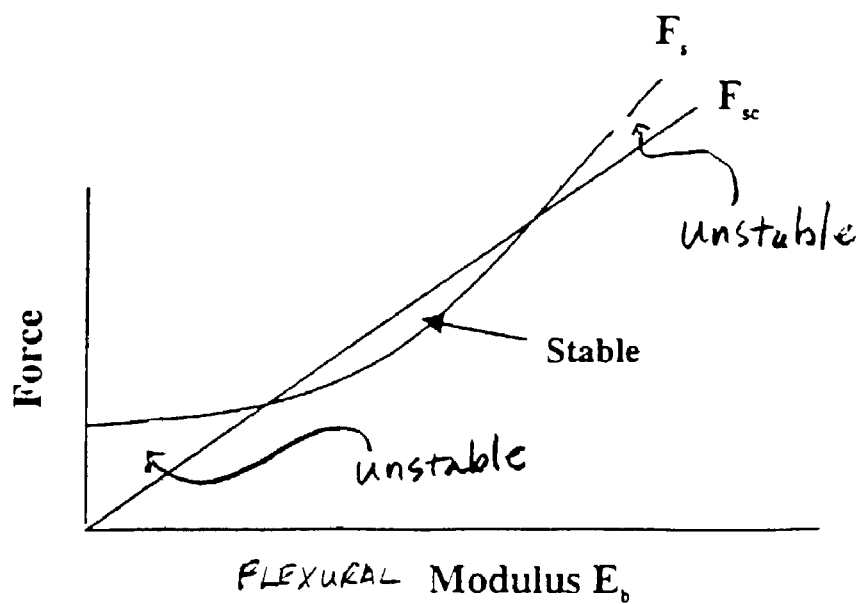
FIG. 1 illustrates, graphically, the relationship between trackability and pushability of a tubular member as a function of flexural modulus thereby illustrating unstable situations where buckling can occur and stable situations where buckling will not occur.
Figure 2:
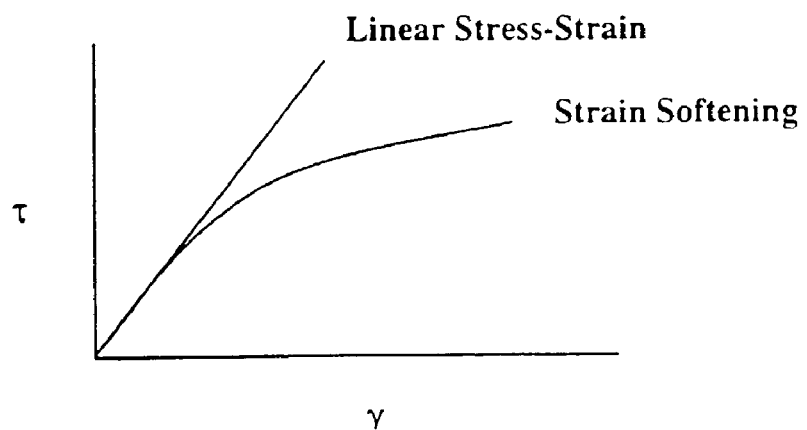
FIG. 2 illustrates, graphically, the relationship between stress and strain for a linear stress-strain tubular member and a strain softening tubular member.

Specifically, flexural modulus ($E_b$) is the ratio of stress to strain within the elastic limit. A non-linear, strain softening structure can be broadly defined as a structure wherein the stress τ exhibits a decreasing dependence on strain γ. This is illustrated in FIG. 2 wherein the "strain softening" curve of the disclosed tubing represents a tubing that takes less force ($F_s$) to push the tubing through a tortuous path than the linear stress-strain tubing of the prior art.

Figure 3A:
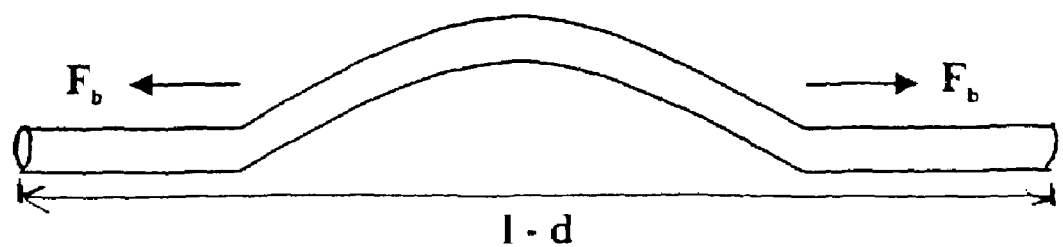
FIG. 3A is a plan view of a piece of tubing that has been bent or curved thereby reducing its effective length from 1 to 1-$d$.
Figure 3B:
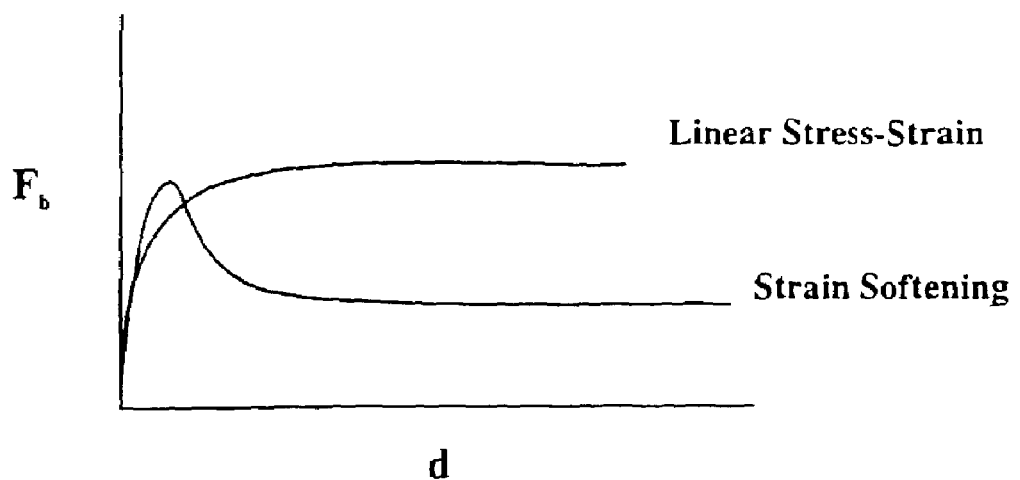
FIG. 3B illustrates, graphically, bending force $F_b$ versus bending amount or length reduction d for the strain softening tubing disclosed herein and for a conventional linear stress-strain tubing.

Furthermore, stress-strain properties have a large effect on the forces developed when a tubing sample traverses a tortuous path. For example, FIGS. 3A and 3B illustrate the forces that arise when a section of the tubing of length 1 undergoes a bending force $F_b$ and is compressed or bent thereby reducing the length of the tubing by an amount d. Specifically, in FIG. 3A, the tubing of an overall length 1 has a reduced length 1-$d$ due to the bending shown in FIG. 3A. In FIG. 3B, as d approaches zero, the strain softening tubing disclosed herein is stiff. As the tubing bends, $F_b$ goes down thereby lowering $F_s$ meaning that the force required to push the bent tubing disclosed herein through a tortuous path is less than the linear stress-strain tubing of the prior art.

Figure 4:
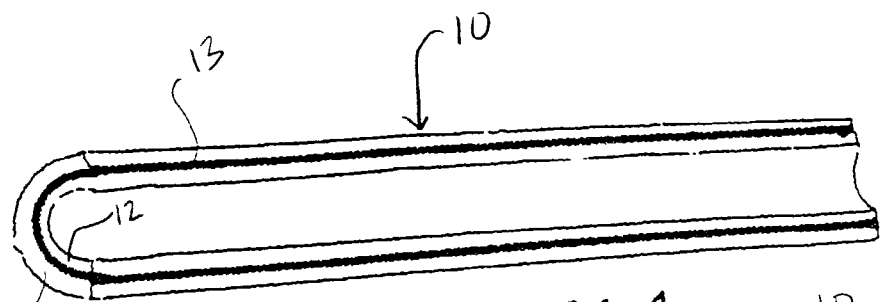
FIG. 4 is a partial perspective view of a tubular member made in accordance with the disclosure with a section removed.

Turning to FIG. 4, a tubular member 10 is illustrated which includes two distinct components including a first component or material disposed as inner and outer layers 11 and 12 and a second component or material disposed as a middle layer 13. The use of two distinct materials provides for improved functional performance. More specifically, the stress-strain behavior, or more specifically, the strain softening behavior as graphically illustrated in FIGS. 2 and 3A, of the tubing 10 has improved trackability, tip force transmission and reduced guide catheter push-out forces. The use of the two materials of the layers 11, 13 and 12 result in the tubing 10 exhibiting non-linear strain softening stress-strain properties. As a result, the tubing 10 allows for increased buckling strength without adversely affecting the flexibility of the tubing 10.

Figure 5:
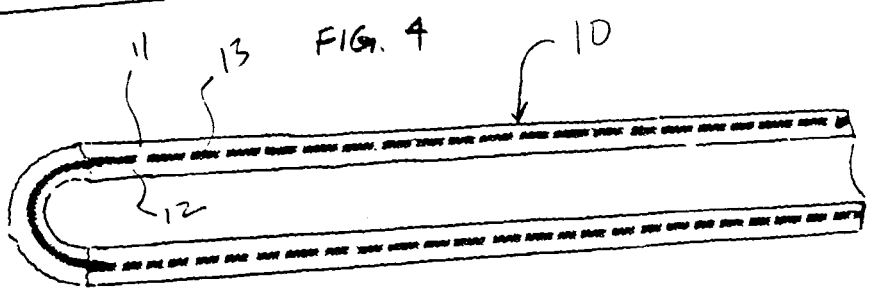
FIG. 5 is a partial perspective view of the tubular member shown in FIG. 4 after the second material has been fractured.

To achieve this result, the tubing 10 includes a first material for the layers 11, 12 which have a low flexural modulus $E_b$ and a high break elongation. Further, the tubing 10 has a second material to the layer 13 which has a high flexural modulus $E_b$ and a low break elongation. To further enhance the performance of the tubing 10, the second material 13 is fractured as shown in FIG. 5.

The low flexural modulus of the first material preferably ranges from about 100 to about 2,000 mPa and the high flexural modulus of the second material preferably ranges from about 2,000 to about 20,000 mPa. The high break elongation of the first material preferably ranges from about 100 to about 1,000%, while the low break elongation of the second material preferably ranges from about 0.1 to about 10%.

Thus, the stiffer more brittle material of the layer 13 has a relatively low break elongation characteristic. Thus, the material for the layer 13 may include, glassy, amorphous material such as polystyrenes and amorphous polyamides. The brittle component of the layer 13 may also include semicrystalline thermoplastics, one of many examples being polyamide-66. Further, the second material may also include various liquid crystalline polymers, such as thermotropic liquid crystalline polymers of aromatic main chain polyesters. Mixtures of the above are also possible.

Additionally, the brittle component of the layer 13 may also include various inorganic glasses formed by the condensation of alkoxides, such as silanes. The material of the layer 13 may also be a blend of a thermoplastic resin with a filler which exhibits brittle behavior. The filler may be another brittle polymer or inorganic material as described above. In addition, such a filler may be a nano-structured material. The filler may also include metals and magnetic particles. Mixtures of the above may also be employed.

The more flexible component of the layers 11, 12 may include thermoplastic resins known for flexible catheter applications. Examples include polyamide-12, polyamide-polyether block copolymers, polyester-polyether block copolymers, polyolefins, polyurethanes and others as well as mixtures of the above. Those skilled in the art will be aware of other possibilities as well.

Figures 6, 9:
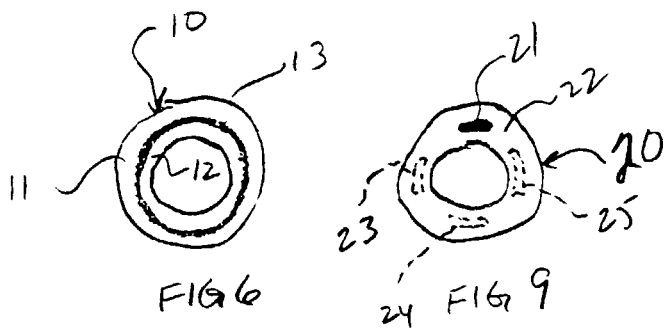
FIG. 6 is an end view of the tubular member of FIG. 4.
FIG. 9 is an end view of the tubular member shown in FIG. 7.
Figure 7:
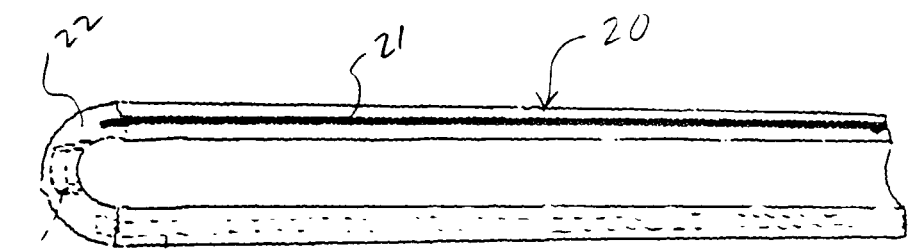
FIG. 7 is a partial perspective view of a tubular member made in accordance with the disclosure illustrating one strip of second material and two additional strips of second material shown in phantom and with a portion of the tubular member removed.
Figure 8:
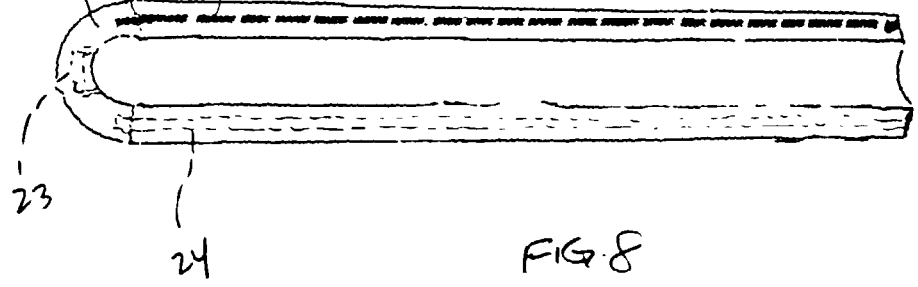
FIG. 8 is a partial perspective of the tubular member of FIG. 7 after the second material has been fractured.

The combination of the flexible material for the layers 11, 13 and the brittle more rigid material of the layer 13 may be combined in a number of ways, in addition to the inner and outer layers 11, 12 and middle layer 13 configuration of FIGS. 4-6. Specifically, as seen in FIGS. 7-9, the tubing 20 may include an elongated strip 21 of the more rigid, brittle material disposed within a layer 22 of the more flexible material. Additional elongated strips may also be provided and are shown in phantom at 23, 24. Again, the brittle material may then be fractured as shown in FIG. 8. An additional fourth strip is shown in phantom at 25 in FIG. 9. The brittle material may also be provided in a series of concentric rings as illustrated generally by the fractured layer 13 of FIG. 5.

The more brittle, rigid material of the layers 13 or strips 21, 23-25 may be fractured by stretching the tubing 10, 20 or otherwise applying a tensile force to the tubing 10, 20. Further, the fracturing may be performed in vivo within a patient.

The two materials may be coextruded together to form a shaft. The shaft may then be cooled. The cool shaft may then be stretched to provide the fracturing of the second material or the shaft may then be inserted into a patient and stretched in vivo for fracturing. The finished shaft may then be used to perform a medical procedure within the vascular system of the patient prior to removing the shaft from the patient.

Although specific embodiments and methods have been described, workers skilled in the art will realize that changes may be made in form and detail without departing from the spirit and scope of this disclosure.

What is claimed is:

1. A medical tubing comprising: a first material extending between a proximal end and a distal end of the tubing and defining a lumen of the tubing and an outer surface of the tubing; and a second material extending between at least a portion of a distance between the proximal end and the distal end of the tubing and embedded in the first material, the second material being fractured into a plurality of juxtaposed pieces.

2. The medical tubing of claim 1, wherein the first material has a low flexural modulus and a high break elongation.

3. The medical tubing of claim 2, wherein the low flexural modulus of the first material ranges from about 100 mPa to about 2,000 mPa.

4. The medical tubing of claim 2, wherein the high break elongation of the first material ranges from about 100% to about 1,000%.

5. The medical tubing of claim 2, wherein the low flexural modulus of the first material ranges from about 100 mPa to about 2,000 mPa and the high break elongation of the first material ranges from about 100% to about 1,000%.

6. A medical tubing comprising: a first material extending between a proximal end and a distal end of the tubing and defining a lumen of the tubing and an outer surface of the tubing; and a second material extending between at least a portion of a distance between the proximal end and the distal end of the tubing and embedded in the first material, the second material being fractured, wherein the second material has a high flexural modulus and a low break elongation.

7. The medical tubing of claim 6, wherein the high flexural modulus of the second material ranges from about 2,000 mPa to about 20,000 mPa.

8. The medical tubing of claim 6, wherein the low break elongation of the second material ranges from about 0.1% to about 10%.

9. The medical tubing of claim 6, wherein the high flexural modulus of the second material ranges from about 2,000 mPa to about 20,000 mPa and the low break elongation of the second material ranges from about 0.1% to about 10%.

10. A medical tubing comprising: a first material extending between a proximal end and a distal end of the tubing and defining a lumen of the tubing and an outer surface of the tubing; and a second material extending between at least a portion of a distance between the proximal end and the distal end of the tubing and embedded in the first material, the second material being fractured, wherein the first material has a low flexural modulus and a high break elongation, and the second material has a high flexural modulus and a low break elongation.

11. The medical tubing of claim 10, wherein the low flexural modulus of the first material ranges from about 100 mPa to about 2,000 mPa and the high break elongation of the first material ranges from about 100% to about 1,000% and the high flexural modulus of the second material ranges from about 2,000 mPa to about 20,000 mPa and the low break elongation of the second material ranges from about 0.1% to about 10%.

12. The medical tubing of claim 1, wherein the first material forms a first layer defining the lumen of tubing, the second material forms a second layer, and the first material forms a third layer which comprises the outer surface of the tubing; wherein the second layer is disposed between the first and second layers.

13. The medical tubing of claim 1, wherein the tubing comprises a longitudinal axis, and the second material comprises at least one strip of material extending along the longitudinal axis of the tubing.

14. A medical tubing comprising: a first material extending between a proximal end and a distal end of the tubing and defining a lumen of the tubing and an outer surface of the tubing; and a second material extending between at least a portion of a distance between the proximal end and the distal end of the tubing and embedded in the first material, the second material being fractured, wherein the tubing comprises a longitudinal axis, and the second material comprises a plurality of circumferential rings that are axially spaced apart and that extend along the longitudinal axis of the tubing.

15. A medical tubing comprising: a first material extending between a proximal end and a distal end of the tubing and defining a lumen of the tubing and an outer surface of the tubing; and a second material extending between at least a portion of a distance between the proximal end and the distal end of the tubing and embedded in the first material the second material being fractured, wherein the second material comprises a plurality of domains.

16. A medical tubing comprising: a first material extending between a proximal end and a distal end of the tubing and defining a lumen of the tubing and an outer surface of the tubing; and a second material extending between at least a portion of a distance between the proximal end and the distal end of the tubing and embedded in the first material, the second material being fractured, wherein the tubing is a single layer blend of the first material and the second material.

17. A medical tubing comprising: a first material extending between a proximal end and a distal end of the tubing and defining a lumen of the tubing and an outer surface of the tubing, the first material having a low flexural modulus and a high break elongation; and a second material extending between at least a portion of a distance between the proximal end and the distal end of the tubing and embedded in the first material, the second material having a high flexural modulus and a low break elongation, and the second material being fractured.

18. The medical tubing of claim 17, wherein the first material forms a first layer defining the lumen of tubing, the second material forms a second layer, and the first material forms a third layer which comprises the outer surface of the tubing; wherein the second layer is disposed between the first layer and the second layer.

19. The medical tubing of claim 17, wherein the tubing comprises a longitudinal axis, and the second material comprises at least one strip of material extending along the longitudinal axis of the tubing.

20. The medical tubing of claim 17, wherein the tubing comprises a longitudinal axis, and the second material comprises a plurality of circumferential rings that are axially spaced apart and that extend along the longitudinal axis of the tubing.

21. The medical tubing of claim 17, wherein the second material comprises a plurality of domains.

22. The medical tubing of claim 17, wherein the tubing is a single layer blend of the first material and the second material.

23. The medical tubing of claim 17, wherein the low flexural modulus of the first material ranges from about 100 mPa to about 2,000 mPa and the high break elongation of the first material ranges from about 100% to about 1,000% and the high flexural modulus of the second material ranges from about 2,000 mPa to about 20,000 mPa and the low break elongation of the second material ranges from about 0.1% to about 10%.

* * * * *